US00PP34371P2

(12) United States Plant Patent
Hansen

(10) Patent No.: US PP34,371 P2
(45) Date of Patent: Jun. 21, 2022

(54) ***MONARDA* PLANT NAMED 'LEADING LADY AMETHYST'**

(50) Latin Name: ***Monarda* hybrid**
Varietal Denomination: Leading Lady Amethyst

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/300,862

(22) Filed: Nov. 29, 2021

(51) Int. Cl.
*A01H 5/02* (2018.01)
*A01H 6/50* (2018.01)

(52) U.S. Cl.
USPC ..... Plt./455
CPC ..... *A01H 6/50* (2018.05)

(58) Field of Classification Search
USPC ..... Plt./455
CPC ..... A01H 6/50; A01H 5/02
See application file for complete search history.

*Primary Examiner* — Keith O. Robinson

(57) ABSTRACT

The new and distinct cultivar of ornamental cultivar of hybrid ornamental Bee Balm plant named *Monarda* 'Leading Lady Amethyst' with deep-green, moderately-glossy, powdery mildew-tolerant foliage, flower heads of light amethyst-purple with lighter interiors effectively showing off the dark purple spots on the inner surface. The plant habit is short, compact, tightly clumping and winter-hardy, useful in the landscape as a specimen, en masse, or as a containerized plant.

1 Drawing Sheet

BOTANICAL DESIGNATION AND CULTIVAR DENOMINATION

Botanical classification: *Monarda* hybrid.
Variety denomination: 'Leading Lady Amethyst'.

STATEMENT REGARDING PRIOR DISCLOSURES UNDER 37 CFR 1.77(b)(6)

The first public disclosure of the claimed plant, in the form of a sale, was made by Walters Gardens, Inc. on Jul. 12, 2021 to Natorp's Nursery. Prior to that, on Dec. 1, 2020 the claimed plant was displayed with a non-enabling photograph and brief description in a website operated by Walters Gardens, Inc., and on May 21, 2021 as a non-enabling photograph and brief description in the "Walters Gardens 21-22 Catalog" by Walters Gardens, Inc., who obtained the plant and all information relating thereto, from the inventor. No plants of *Monarda* 'Leading Lady Amethyst' have been sold, in this country or anywhere in the world, nor has any disclosure of the new plant been made more than one year prior the filing date of this application, and such sale or disclosure within one year was either derived directly or indirectly from the inventor.

BACKGROUND OF THE INVENTION

The present invention relates to the new and distinct cultivar of Bee Balm, botanically known as *Monarda* 'Leading Lady Amethyst', and hereinafter also referred to solely by the cultivar 'Leading Lady Amethyst' or the "new plant." *Monarda* 'Leading Lady Amethyst' was the result of a controlled self-pollination in the summer of Jul. 17, 2015 in trial garden at a wholesale perennial nursery in Zeeland, Mich., USA. The parent is a proprietary, unnamed, unreleased hybrid known as 14-57-1 (not patented). The new plant was separated out for further evaluation in the summer of 2017 in the seedling field of the same nursery and assigned the breeder code 15-51-1. The new plant is the result of a planned breeding program of the inventor to produce new colors of flowers with superior mildew resistance, and improved compact habit. The new plant has been asexually propagated since 2017 by division and by basal stem cuttings at the same nursery in the greenhouses in Zeeland, Mich., and the subsequent generations of asexually propagated plants found to be stable and identical to the original selection.

BRIEF SUMMARY OF THE PLANT

*Monarda* 'Leading Lady Amethyst' is unique from its parents and all other Bee Balm plants known to the inventor. The nearest comparison cultivars known to the inventor are 'Leading Lady Plum' U.S. Plant Pat. No. 26,447, 'Pardon My Lavender' U.S. Plant Pat. No. 28,770 and 'Pardon My Lavender II' U.S. Plant patent application Ser. No. 17/300,859.

'Leading Lady Plum' has a similar habit with magenta-purple flowers with darker spots. 'Pardon My Lavender' has flowers of lavender-purple color without darker spots and is slightly taller in habit and not as resistant to powdery mildew. 'Pardon My Lavender II' has a slightly taller habit, but the flower color is a darker lavender purple and lacks the dark spots on the petals. 'Leading Lady Amethyst' flowers earlier than 'Pardon My Lavender' and 'Pardon My Lavender II'.

The parent is more open and taller in habit than the new plant and is lighter amethyst-lavender in flower color.

*Monarda* 'Leading Lady Amethyst' is distinct from all Bee Balm plants known to the inventor. The following are traits of the new plant that in combination distinguish it from all other Bee Balm known to the inventor:

1. Short, compact, clumping, upright mound that is winter-hardy habit;
2. Lanceolate to cordate, deep-green, moderately-glossy, powdery mildew-tolerant foliage;
3. Compact, light amethyst-purple flowers with lighter interiors effectively show off the dark purple spots;
4. Flowering over a five-week-long period beginning early June;
5. Flowering in dense verticils.

BRIEF DESCRIPTION OF THE DRAWINGS

The photographs of the new plant demonstrate the unique traits of *Monarda* 'Leading Lady Amethyst' and the overall appearance of a three-years-old plant in the full sun trial garden of a nursery in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
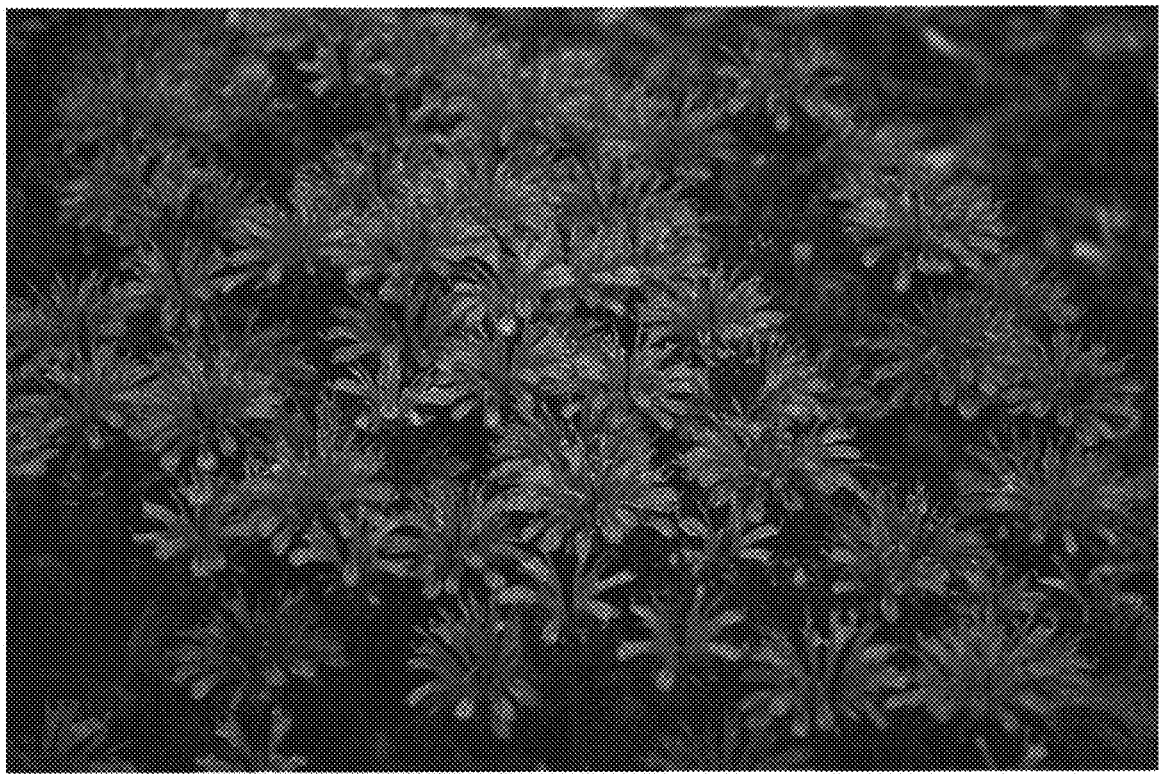
FIG. 1 shows the habit of the new plant in full flower.
Figure 2:
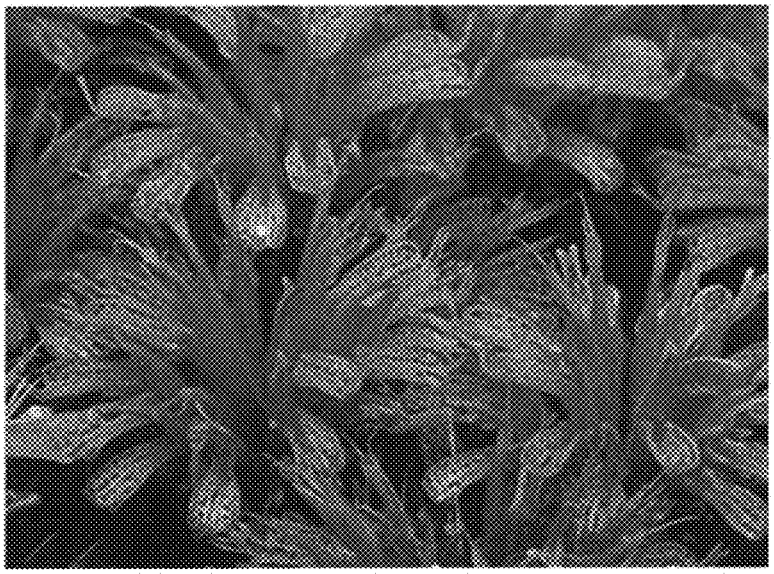
FIG. 2 shows a close-up of the flower of the new plant.

The following descriptions and color references are based on the 2015 edition of The Royal Horticultural Society Colour Chart except where common dictionary terms are used. *Monarda* 'Leading Lady Amethyst' has not been observed under all possible environments. The phenotype may vary slightly with different growing environments such as temperature, light, fertility, soil pH, moisture and maturity levels, but without any change in the genotype. The following observations and size descriptions are based on two-year-old plants grown in a trial garden at a nursery in Zeeland, Mich. with supplemental fertilizer and water as needed.

Botanical classification: *Monarda* hybrid;

Parentage: The parent is 14-57-1, an unreleased proprietary hybrid;

Plant habit: Hardy herbaceous perennial, dense, upright mound, producing multiple stems spreading by short rhizomes near the base of the stems; foliage up to 32.0 cm tall, flowering to 38.0 cm tall and 47.0 cm wide; flowering begins early June in Michigan and continuing for about 5 weeks;

Propagation: Stem cuttings;

Time to produce finished crop in 3.8-liter pots: About 7 to 9 weeks; moderate rate of growth;

Root: Fine, fibrous and freely branching; color creamy white to tan depending on soil type;

Leaves: Simple; lanceolate to cordate; opposite; margin serrated with 10 to 12 teeth per side, to 2 mm wide and 1.5 mm long; puberulent adaxial and abaxial; moderately lustrous adaxial, matte abaxial; acute apex; cordate to rounded base; to about 8.0 cm long and 2.8 cm wide, average about 5.5 cm long and 2.4 cm wide near base;

Leaf color: Young expanding leaves adaxial nearest RHS 146B, abaxial nearest RHS 146C; mature leaves adaxial between RHS 137A and RHS 136A, abaxial between RHS 138A and RHS 137C; without significant anthocyanins;

Foliage fragrance: Pleasant lemony-herbal;

Veins: Pinnate; glabrous and slightly sunken adaxial, micropuberulent and costate abaxial;

Vein color: Young adaxial midrib between RHS 146D and RHS 148C and primary veins nearest RHS 146C; abaxial midrib nearest RHS 145C and primary veins nearest RHS 146C; mature adaxial midrib nearest RHS 146D, primary veins variable between RHS 145C and RHS 146D, mature abaxial midrib nearest RHS 146D and primary veins nearest RHS 146C;

Petiole: Glabrescent adaxial and puberulent abaxial, slightly concaved above; to about 7.0 mm long and 2.5 mm across at base; strength medium;

Petiole color: Adaxial nearest RHS146A and abaxial nearest RHS 146D;

Stems: Quadrangular; glabrous; about 3.0 mm across at base; about 8 per plant; naturally branched at upper nodes; average 3.2 cm between nodes greater distally; 9 to 12 nodes per stem; average length about 38 cm; average internode length 3.5 cm;

Stem color: Nearest RHS 146B with slight anthocyanin blushing of nearest RHS 187B; nodes same color as surrounding stem;

Flowers: Single, bilabiate flowers arranged in mostly terminal verticils forming globular inflorescence head about 70.0 mm across and 28.0 mm tall, opening from the center and progressing outwardly and down; attitude outwardly to upwardly; individual flowers to about 34.0 mm long to exserted stigma, corolla to 29 mm long, 14.0 mm tall and about 6.0 mm across; individual flowers persisting about 5 days in Michigan; numerous, about 150 to 200 flowers per terminal head, fewer per axillary head; 100 inflorescences with open flowers at one time;

Flower fragrance: Moderately spicy;

Buds one to two days prior to opening: Clavate, arcuate downward; glandular to puberulent; about 25.0 mm long and 3.5 mm across and 4.0 mm tall;

Bud color: Dorsal lip distally nearest RHS 77A, side portion nearest RHS N80B; ventral lip lower and distal portion nearest RHS 76B with spotted undertone of nearest RHS N77A;

Petals: Bilabiate; arcuate downward; basal 18.0 mm fused into tube; split in two in the distal 11.0 mm; abaxial glandular to puberulent except basal 12 mm of abaxial and adaxial glabrous; self-cleaning;

Upper labium: Folded in distal portion, about 11.0 mm long from fusion to acute emarginate apex, 2.0 mm tall, 2.0 mm across at base;

Lower labium: About 15.0 mm long from fusion to apex, 3.5 mm wide at fusion and 7.5 mm wide a lobes when flattened, apex comprising three lobes including two side lobes about 1.0 mm long and 3.0 mm across with rounded apex; center lobe bent upwardly at base, about 4.0 mm long and 2.0 mm wide with emarginate apex cleft about 1.0 mm deep; main portion with darker spots between 0.2 mm and 1.0 mm across;

Petal color: Upper labium adaxial basal 4.0 mm nearest RHS NN155B, distally nearest RHS N80A, abaxial basal 4.0 mm nearest RHS NN155B, distally between RHS 83A and RHS N81A; lower labium adaxial surface nearest RHS N81B at margins and nearest RHS 72A near center distal portion, adaxial middle between RHS N78C and RHS N78D with spots nearest RHS 79B; abaxial distal 15 mm portion nearest RHS N81 C and middle portion nearest RHS N78B with spots showing through of nearest moderate undertone of nearest RHS 79B; corolla tube adaxial and abaxial proximal 4.0 mm nearest RHS NN155C;

Androecium: Two; adnate inner corolla tube in basal portion;

*Filaments*.—Two; curved downward; adnate the inner corolla tube in the basal 16.0 mm and free in the distal 16.0 mm; about 0.5 mm diameter; color in free portion nearest RHS N80B, color in adnate portion nearest RHS 84B.

*Anther*.—Oblong elliptic; dorsifixed; longitudinal; fused together; 3.0 mm long by 0.7 mm wide; color nearest RHS N79C.

*Pollen*.—Abundant, elliptic to globose, less than 0.1 mm; color nearest RHS 10A.

Gynoecium: One; superior; about 30.0 mm long;

Pistil: One per flower; exserted about 5.0 mm beyond upper labium when mature;

Style: Cylindrical; glabrous; about 29.0 mm long and about 0.3 mm diameter; arcuate inside upper labium; color nearest RHS 79C in distal 5.0 mm transitioning to nearest RHS NN155C in middle and basal portion;

Stigma: Unevenly bifid in the distal 1.0 mm and about 0.2 mm diameter; color nearest RHS 79A;

Ovary: Conical; about 1.0 mm tall by 0.75 mm diameter; color nearest RHS 145D;

Calyx: Tubular; consisting of five fused sepals; about 9.0 mm long and 2.0 mm diameter at apex;

Sepals: Five; lanceolate; narrowly acute apex; basal 8.0 mm fused forming calyx tube, free in distal 1.0 mm; margin ciliolate; about 9.0 mm long and 2.0 mm across at fusion; glabrous abaxial, glabrous adaxial except throat pubescent; persistent;

Sepal color: Adaxial and abaxial distal 2.0 mm nearest RHS 187A, middle abaxial fused portion nearest RHS 146D and abaxial basal 1.0 mm nearest RHS 158B; adaxial basal 1.0 mm portion nearest RHS 158B and between base and free apical portion nearest RHS 76B with spotted undertone of nearest RHS N77A;

Foliar bracts: Typically one set of five to seven large bracts on the outside per inflorescence and one set of six smaller bracts in the middle and one set of about 20 to 28 smaller narrow bracts on the inside below each inflorescence; outer bracts lanceolate with acute apex and attenuate sessile base, micro-ciliolate margin, glabrous adaxial, puberulent abaxial, flat to coarsely wavy, matte adaxial and abaxial, to 48.0 mm long and 18.0 mm wide in middle; middle six bracts linear with narrowly acute apex and truncate base, ciliolate margin, glabrous adaxial and micro-puberulent abaxial, to about 22.0 mm long and 5.0 mm across near middle, innermost bracts linear, narrowly acute apex and truncate base, ciliolate margin, adaxial and abaxial glabrous, to about 17.0 mm long and 2.5 mm across at base;

Foliar bract color: Outer bract adaxial between RHS 187A and RHS N186B distally transitioning to nearest RHS NN137B in middle and RHS 145B at base, midrib nearest RHS 186A, color abaxial nearest RHS 138B with midrib nearest RHS 145C with variable blush of nearest RHS 187B; middle six bracts adaxial color distal nearest RHS 187A, middle portion nearest RHS 137B with midrib nearest RHS 186A and base nearest RHS145D, abaxial color nearest 146C in middle with apex strongly blushed with RHS 187A and base nearest RHS 145D; innermost bracts distally adaxial and abaxial nearest RHS 187B and proximally adaxial and abaxial transitioning to nearest RHS 145D at base;

Pedicel: Glabrous, cylindrical; to about 1.5 mm long and 0.7 mm diameter;

Pedicel color: Nearest RHS 195B;

Peduncle: Stiff, strong, erect, glabrous, quadrangular; to about 3.0 mm across and average 45.0 mm long above node; about 100 per plant; naturally branched at nodes;

Peduncle color: Nearest RHS 146C with slight blushing of nearest RHS 187B;

Fruit: Typically one or two, rarely four, glabrous, lustrous, ellipsoidal nutlet; about 1.2 mm long and 0.7 mm wide; color between RHS 165A and RHS 166A;

Hardiness: The new plant grows best with plenty of moisture and adequate drainage; hardy to at least from USDA zone 4 through 8.

Disease and pest resistance: Demonstrated greater than average powdery mildew tolerance of *Erysiphe necator* in side-by-side comparison with other *Monarda*.

I claim:

1. A new and distinct cultivar of hybrid ornamental Bee Balm plant named *Monarda* 'Leading Lady Amethyst', as herein described and illustrated.

* * * * *